US010716492B2

(12) United States Patent
Filipowicz

(10) Patent No.: US 10,716,492 B2
(45) Date of Patent: Jul. 21, 2020

(54) QUADRUPED LAMENESS DETECTION

(71) Applicant: Bay West Veterinary Surgery, Inc., Woodside, CA (US)

(72) Inventor: Dean Filipowicz, Woodside, CA (US)

(73) Assignee: Bay West Veterinary Surgery, Inc., Woodside, CA (US)

(*) Notice: Subject to any disclaimer, the term of this patent is extended or adjusted under 35 U.S.C. 154(b) by 0 days.

(21) Appl. No.: 15/942,382

(22) Filed: Mar. 30, 2018

(65) Prior Publication Data
US 2019/0298226 A1 Oct. 3, 2019

(51) Int. Cl.
*A61B 5/103* (2006.01)
*G01L 5/00* (2006.01)
*A01K 29/00* (2006.01)
*A61B 5/00* (2006.01)
*A61D 99/00* (2006.01)
*A61B 5/11* (2006.01)
(Continued)

(52) U.S. Cl.
CPC .......... *A61B 5/1038* (2013.01); *A01K 29/005* (2013.01); *A61B 5/0024* (2013.01); *A61B 5/112* (2013.01); *A61B 5/6807* (2013.01); *A61D 99/00* (2013.01); *G01L 5/0052* (2013.01); *A61B 2503/40* (2013.01); *H04L 69/18* (2013.01); *H04W 4/80* (2018.02); *H04W 84/12* (2013.01)

(58) Field of Classification Search
None
See application file for complete search history.

(56) References Cited

U.S. PATENT DOCUMENTS 5,736,656 A 4/1998 Fullen et al.
8,379,639 B2 2/2013 Dutta et al.
(Continued)

FOREIGN PATENT DOCUMENTS

CN 101380235 B 12/2010

OTHER PUBLICATIONS

The International Searching Authority, "Search Report" in application No. PCT/US2019/023947, dated Apr. 22, 2019, 11 pages.
(Continued)

*Primary Examiner* — Matthew Kremer
(74) *Attorney, Agent, or Firm* — Elliot H. Karlin; Hickman Palermo Becker Bingham LLP

(57) ABSTRACT

Systems and methods for detecting lameness in a limb of an animal are described herein. In an embodiment, a lameness detection system comprises a plurality of wearable footwear elements. Each of the footwear elements comprises a housing that is configured to fit snugly on a paw of the animal during ordinary gait. Each of the footwear elements comprise a sensor or matrix of sensors that is configured to detect and generate data representative of pressure or force exerted by the paw on a ground surface. Each footwear element additionally comprises a wireless transceiver that is configured for short-distance communication of the data captured by the sensors. The system further comprises a computing device with a wireless transceiver configured to communicate with the transceivers of the footwear elements and instructions which, when executed by the computing device, cause the computing device to analyze lameness in a limb of the animal based on data received from the sensors.

10 Claims, 5 Drawing Sheets

(51) Int. Cl.
  *H04L 29/06* (2006.01)
  *H04W 4/80* (2018.01)
  *H04W 84/12* (2009.01)

(56) References Cited

U.S. PATENT DOCUMENTS

| | | | |
|---|---|---|---|
| 2007/0202478 A1* | 8/2007 | Al-Obaidi | A61B 5/1038 434/247 |
| 2009/0240171 A1* | 9/2009 | Morris Bamberg | A61B 5/1038 600/595 |
| 2012/0253234 A1* | 10/2012 | Yang | A61B 5/1038 600/595 |
| 2012/0291564 A1 | 11/2012 | Amos et al. | |
| 2013/0185003 A1* | 7/2013 | Carbeck | A43B 3/0005 702/41 |
| 2013/0211290 A1* | 8/2013 | Lee | A43B 3/0005 600/592 |
| 2013/0213144 A1 | 8/2013 | Rice et al. | |
| 2013/0213147 A1 | 8/2013 | Rice et al. | |
| 2014/0155785 A1* | 6/2014 | Haas | A61B 5/1038 600/595 |
| 2014/0207374 A1 | 7/2014 | Taylor, Jr. et al. | |
| 2014/0222173 A1 | 8/2014 | Giedwoyn et al. | |
| 2014/0277631 A1 | 9/2014 | Rice et al. | |
| 2016/0192619 A1* | 7/2016 | Gibbs | A01K 5/00 119/61.57 |
| 2017/0095206 A1* | 4/2017 | Leib | G16H 40/63 |
| 2017/0262599 A1* | 9/2017 | Grisel | G16H 50/20 |
| 2018/0116560 A1* | 5/2018 | Quinn | A61B 5/1121 |

OTHER PUBLICATIONS

Current Claims in application No. PCT/US2019/023947, dated Apr. 2019, 5 pages.

\* cited by examiner

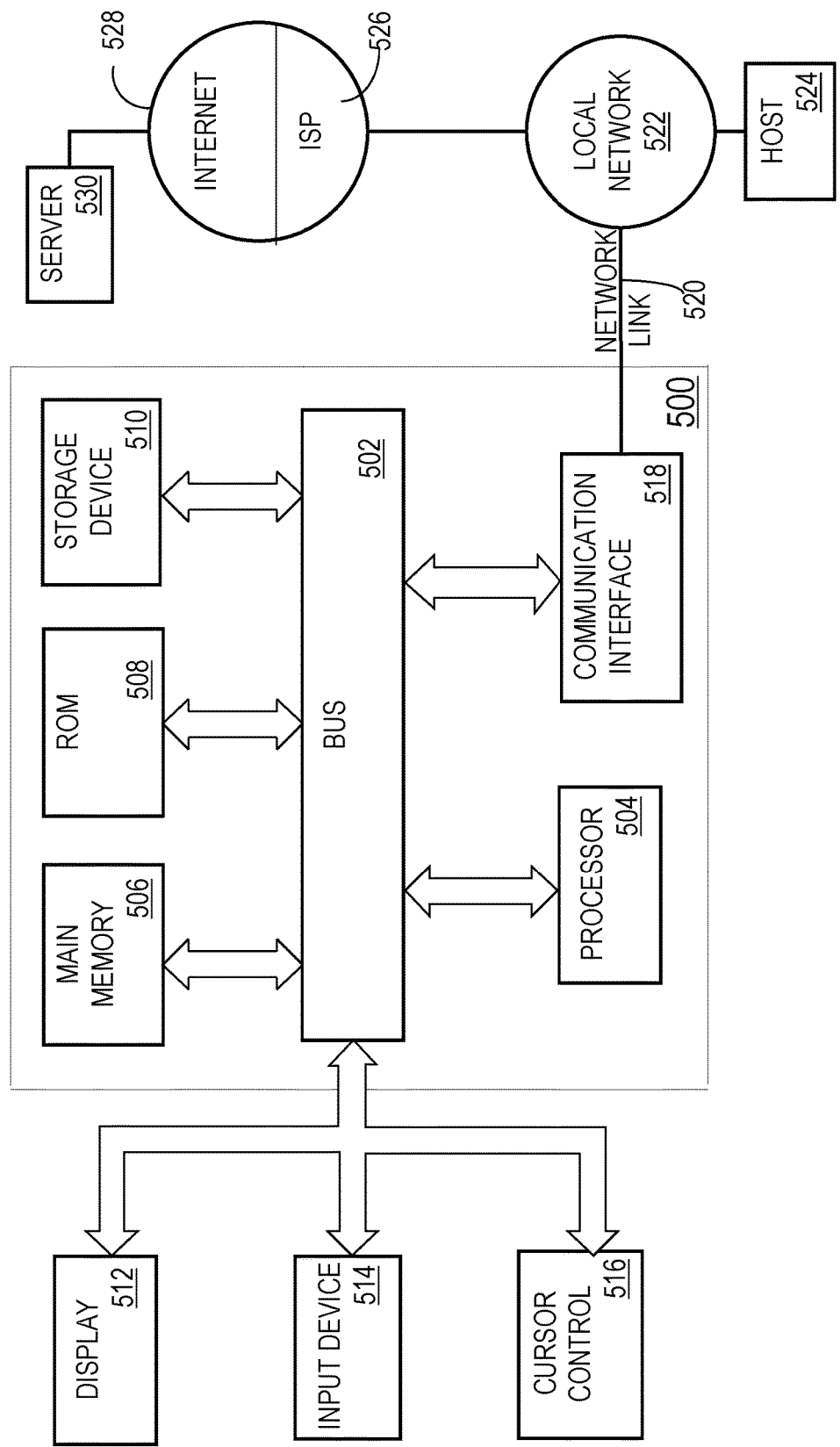

QUADRUPED LAMENESS DETECTION

FIELD OF THE DISCLOSURE

The present disclosure generally relates to data processing systems using wireless networks and wearable sensors. The disclosure relates more specifically to computer systems linked to sensors for the purpose of detecting deviations from symmetry in the use of limbs of an animal to identify and chronicle changes in lameness.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Lameness is a symptom of common musculoskeletal injuries and/or disease in quadruped animals such as domestic dogs and cats. For example, various kinds of ligament and tendon injuries, degenerative joint diseases, insidious bone diseases and other ailments may be manifested in lameness. In this context, lameness refers to the inability of an animal to walk in a normal fashion or to bear full weight on all the limbs in the manner typically observed or experienced in a healthy condition.

However, at present, detecting lameness usually is performed in ways that have significant drawbacks. A first approach involves visual observation and estimation of gait or movement followed by evaluation of an animal's response to stimulus. This approach involves subjective individual analysis that is prone to error and usually only can identify large changes in lameness and/or load bearing starting at higher grades of lameness. It is inherently non-scientific and imprecise.

Another approach involves using a stationary force plate or force pad, alone or in conjunction with secondary quantitative analysis such as goniometry and/or limb circumference measurements. Kinetic analysis based on data from a force plate can be used to generate force time curves in three dimensions as well as values for peak vertical force (PVF), defined as the maximum force in the vertical dimension. These data can be used to evaluate craniocaudal direction in the sense of propulsion and braking, and mediolateral direction or turning. However, the data gathering apparatus is costly, esoteric in nature, and requires detailed training of the subject animal to ensure that load cells are struck and velocity is constant. Furthermore, the apparatus does not measure stride length or duration and is difficult to set up.

Force pads can be used for temporospatial gait analysis to indicate the duration of phases of stride, stride velocity, stride length, step length and a total pressure index. Duration of phases of stride refers to distinguishing stance versus swing. Stride length can be measured as the distance between paw strikes of the same limb. Step length can comprise the distance from an aspect of paw strike of one limb to the same aspect of the strike of a paw of a contralateral limb. The total pressure index may be the sum of peak pressure values recorded on the pad from each activated sensor by a paw during mat contact; it is related but not equal to peak vertical force. Force pad apparatus also is costly, requires a large physical space, and is esoteric. Additional forces present during ambulation can interfere with and complicate measurement; examples include forces to change speed, direction or maintain balance. Further, the apparatus only measures total ground reaction forces and not component vectors.

Kinematic gait analysis typically involves using markers affixed to joints and recording the movement of the markers using a video camera, followed by secondary quantitative analysis such as goniometry and/or limb circumference measurements. This approach is costly, difficult or impractical to perform with some animals, and produces data that is not easily repeatable. There can be random error in the data due to skin movement, and creating reference values is not supported.

Based on these deficiencies in current practice, there is a need for an improved easily available apparatus for reliably and precisely quantitating lameness in animals.

SUMMARY

The appended claims may serve as a summary of the invention.

BRIEF DESCRIPTION OF THE DRAWINGS

In the drawings:

FIG. 5 illustrates an example computer system with which embodiments may be implemented.

Figure 1:
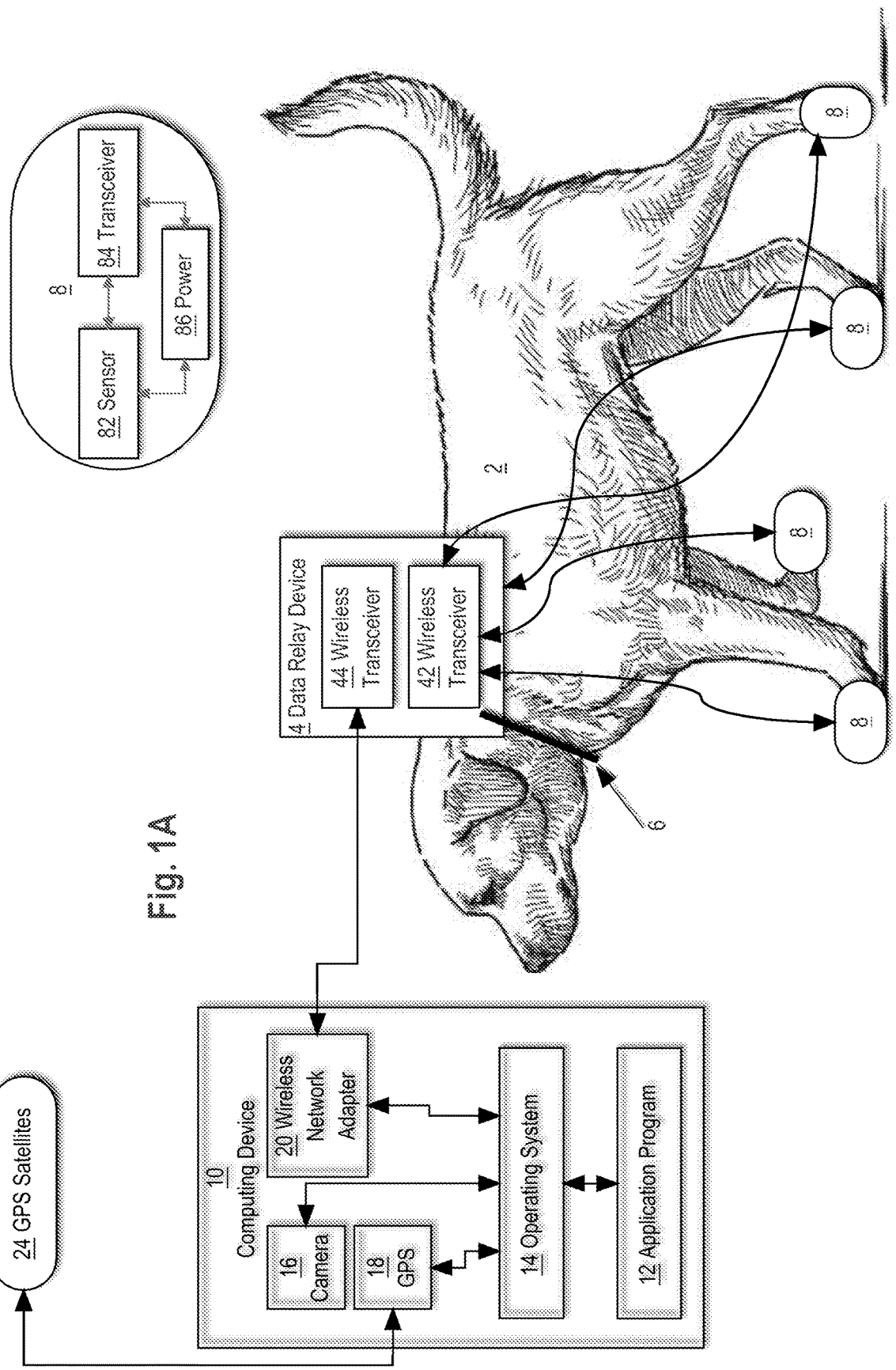
FIG. 1A illustrates an example lameness assessment system, according to one embodiment.
FIG. 1B illustrates internal elements of an example footwear element of FIG. 1A.

The drawings are not to scale.

DETAILED DESCRIPTION

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

General Overview

According to one embodiment, a lameness measurement system comprises a plurality of wearable footwear elements, each comprising a sensor and a short-distance wireless data transmitter, and a computing device having a storage device holding an application program that is programmed to obtain sensor data from the sensors and analyze the sensor data to produce an analysis of lameness of the animal. In some embodiments, the system further comprises a wireless data relay device that is configured to receive sensor data from the sensors via a first wireless networking protocol, to transform the sensor data into electronic messages, optionally with analysis, compression or other operations, and to transmit the transformed sensor data via a second wireless networking protocol to the computing device. In some embodiments, the wireless data relay device is miniature and may be affixed to a collar of the animal. In some embodiments, the computing device is a mobile computing device and the application program is implemented as a compact program or mobile app.

In one embodiment, the system is programmed to indicate acute lameness and/or lameness over time in a quadruped animal. In an embodiment, the system is programmed to monitor progression of recovery or lameness. In an embodiment, input or a first measurement may specify baseline data values for the gait of an animal; in various embodiments, one or more of the baseline data values may be associated with different attributes or tags, such as a particular age or date; an activity such as a race, event or work; or a research project, contract, surgical procedure, or other indicator.

In some embodiments, the data relay device or one of the footwear elements further comprises a global positioning system (GPS) transceiver that is configured or programmed to obtain GPS radio signals from earth orbiting satellites and to compute a geo-spatial position or location position based upon the GPS signals. In such an embodiment, the GPS transceiver may be programmed or configured to accept calls, polls, or other signals from the data relay device, footwear elements or computing device to report then-current geo-location data values such as a pair of latitude-longitude (lat-long) values. These values also may be periodically transmitted without a request or poll signal according to a schedule, such as once per second.

Consequently, in an embodiment, the system permits algorithmic case management in which different options may be explored such as surgery, conservative management, addition of a medication, change of a medication, change of diet, physical therapy or rehabilitation. The system may be programmed to compare alternative case management options.

Embodiments will find utility with surgeons, neurologists, oncologists, rehabilitation providers, and general practitioners, as well as handlers or owners of working animals, owners of animals that have recognized injuries and/or disease, owners of animals that are at risk of injury or disease based on breed or history, and owners of animals that are difficult to handle or transport. Embodiments may also find utility when methods for performing orthopedic exams are inconsistent or inaccurate, such as with cats or small dogs which compensate better for subtle lameness, making the lameness more difficult to visualize or identify. Embodiments can be produced at reasonable cost and are configured for ease of use and ease of understanding. Embodiments provide precise and repeatable data with the introduction of no significant systemic error.

Embodiments are contemplated for use with small quadruped animals such as dogs and cats.

FIG. 1A illustrates an example lameness assessment system, according to one embodiment. In the example of FIG. 1A, a quadruped animal 2 is fitted with a data relay device 4 that is integrated with, affixed to or mounted on collar 6. Animal 2, which is a dog having four (4) paws in the example of FIG. 1A, wears or is fitted with a plurality of footwear elements 8 each comprising a sensor and a wireless transceiver that is capable of wireless data communication with a first wireless transceiver 42 of the data relay device 4, as indicated by arrows joining the footwear elements and the data relay device. While methods are described with respect to four legged animals, embodiments may be applied to animals with less legs, such as amputees, in order to assess possible incipient pathology.

A computing device 10 comprises an application program 12, operating system 14, camera 16, GPS transceiver 18 and wireless network adapter 20. Application program 12 executes on or is hosted by the computing device 10 and is configured or programmed with stored program instructions which when executed cause performing the functions, operations and process steps that are further described in other sections herein. Camera 16 may be integrated into the computing device 10 or arranged as a peripheral that is coupled to the computing device using a parallel data or serial data I/O interface. In one embodiment, camera 16 is controlled by subroutines organized as primitive services of the operating system 14 and that are callable using programmatic calls using a defined API or operating system call facility. GPS transceiver 18 is configured or programmed to communicate wirelessly by radio with GPS satellites 24 in orbital positions around the earth and to calculate a geo-location position of the computing device 10 in terms of latitude, longitude values based on wireless signals from the satellites. The wireless network adapter 20 is communicatively coupled to the data relay device 4 via a second wireless transceiver 44 in the data relay device.

In one embodiment, computing device 10 may be implemented in the manner shown in FIG. 5 and further described in other sections herein. FIG. 1A comprises one configuration of elements for the purpose of providing a clear example. In other configurations, more or less elements may be included. For example, the wireless relay device 4 may communicate with one or more server computers, such as one or more cloud servers, which store received data and communicate with client computing devices. As another example, the wearable elements may include wireless transmitters which send data directly to the computing device 10 without a wireless relay device 4.

Implementation Example—Wearable Elements

FIG. 1B illustrates internal elements of an example footwear element of FIG. 1A. In one embodiment, each footwear element 8 comprises a body or housing that is configured to fit snugly over a foot or paw of the animal 2. In or integrated into the body or housing are a sensor 82, wireless transceiver 84, and power supply 86.

In an embodiment, the footwear elements 8 may comprise shoes, boots or booties with sensors. The footwear elements 8 typically are configured to cause zero to minimal effect on the gait of the animal, or configured so that any effect on gait is the same for each limb. In various embodiments, the footwear elements 8 may be disposable, or constructed of materials that are engineered to last approximately 1 week to 1 year in the typical clinical setting. Different embodiments may comprise a plurality of same-sized footwear elements 8 that are intended for universal use with all animal limbs, or a plurality of different, specifically-sized footwear elements, or fully customized footwear elements that are fitted to a particular species, breed or individual animal.

In various embodiments, footwear elements 8 may comprise sensors configured to be attached to a foot of an animal using different attachment methods. For example, miniaturized inertial motion units may be adhered to the nails of an animal using a glue, epoxy, or other adherence element. As another example a footwear element 8 may comprise sensors within a ring that is to be attached to a toe of an animal.

In various embodiments, each sensor or array of sensors 82 may comprise any of force sensors, pressure sensors or hybrid sensors, inertial motion units, and/or other accelerometers in, on or associated with the footwear elements 8. As an example, force sensors may comprise sheets of material with contact leads for sensing a force and generating an analog electrical signal in response. The force sensors may be configured with a sheet or pressure plate between the foot of the animal and the sensor in order to measure the force placed on the ground by the foot. Additionally or alternatively, a force sensor may be configured with the sensor between the foot and the pressure plate, thereby measuring the ground reactive force on the limb.

In an embodiment, each sensor or sensor array 82 is capable of measuring a total load or total ground reactive force per limb and can compartmentalize the paw strike. In an embodiment, the application program 12 is programmed to collect data values for relative load or impulse of every limb on the same stride. In an embodiment, each sensor 82 is capable of reporting a duration of a foot strike, or the computing device 10 or data relay device 4 is configured or programmed to calculate a duration of a foot strike based upon internal digital electronic clocks and data packets, messages or the content of data received from the sensors.

In an embodiment, sensors 82 comprise dielectric electroactive polymers which provide output proportion to a magnitude of deformation of the polymer. Such sensors may be placed between two plates in order to measure the force with which a foot impacts the ground. In another embodiment, sensors 82 comprises a plurality of pressure sensors arranged in an array, each of which being configured to determine if more than a threshold amount of pressure is imposed on the sensor. With a large array of pressure sensors, a system may compute the force of impact based on a percentage of sensors that activate during the impact.

In various embodiments, the sensors 82 may comprise load cell strain gauges, piezoelectric load cells, resistive sensors or capacitance load cells. When load cell strain gauges are used, there may be four (4) strain gauges coupled using a Wheatstone bridge, or an array of load cells in each footwear element and coupled in parallel.

In one embodiment, each of the footwear elements 8 further comprises an accelerometer, which may be affixed or mounted at or near the hock or carpus. Additionally or alternatively, the accelerometer may be affixed closer to the heel of the foot or nail, which is expected to be the location of greatest change in acceleration of the foot or paw.

In some embodiments, the sensors 82 and/or accelerometer may comprise active electronic devices that are powered using disposable, replaceable or rechargeable batteries as the power supply 86 and that are mounted proximate to the sensors and electrically coupled to them. In some embodiments, the footwear elements may comprise a switch that applies or disconnects power to the sensors; for example, magnetic reed switches may be used to facilitate non-contact switching through a sealed housing, or other external switches such as slide switches, toggles or pushbuttons. In some embodiments, long-life sealed batteries such as lithium-ion batteries may be used and considered essentially disposable. Or, rechargeable batteries may be used with external capacitative charging, charging through a connector to a transformer or other external power supply, and/or charging through kinetic motion of the limb.

Implementation Example—Data Relay Device

In an embodiment, the wireless data relay device 4 may comprise a compact housing that is capable of affixing to or integration with a collar 6, harness, lead, jacket, band, or other item that an animal may wear or carry. In one embodiment, the wireless data relay device 4 comprises a central processing unit or microcontroller, wireless networking transceivers 42, 44, memory devices and programmed firmware that are collectively miniature and capable of integration into the collar 6 or other item. A dongle, capsule or other housing may be used and affixed to the item, or the electronic elements noted above may be in a housing that is sealed within a collar or other item that is capable of use with different animals.

The wireless networking transceivers 42, 44 may be programmed or configured to communicate with the footwear elements 8 and the computing device 10 through wireless network adapter 20. In an embodiment, the transceivers communicate using different wireless protocols. For example, wireless networking transceiver 42 may communicate with footwear elements 8 through short distance wireless communication, such as BLUETOOTH, while wireless networking transceiver 44 communicates through a longer distance wireless communication protocol, such as WIFI, radio frequency, microwave, magnetic coupling, infrared transmission and/or any other means of wireless communication.

The wireless data relay device 4 may additionally include one or more proximity sensors, such as capacitive sensors, photoelectric sensors, inductive proximity sensors, and/or any of the other sensors described herein. Additionally and/or alternatively, the wireless data relay device 4 may comprise one or more sensor targets which can be sensed by one or more proximity sensors on other devices. For example a feeding and/or watering device may include a proximity sensor which is programmed or configured to detect wireless data relay device 4 when within the nominal range. Other embodiments of data relay device 4 may include wired connections for attaching to a computing device. Thus, the data relay device 4 may receive data from the footwear elements and store the data until a wired connection is established between the data relay device 4 and a computing system.

While FIG. 1A depicts both footwear elements 8 and wireless data relay device 4, embodiments may be implemented without wireless data relay device 4. For example, footwear elements 8 may comprise wireless networking transceivers and be programmed or configured to send data directly to a client computing device and/or cloud storage system.

Implementation Example—Application Program

In an embodiment, the application program 12 is configured or programmed to provide real-time visualization of the data that the sensors 82 collect. In one embodiment, the application program 12 is configured or programmed to generate and display a percentage of weight that is bearing on each limb. In another embodiment, the application program 12 is configured or programmed to generate and display relative paw strike force or impulse in relation to the contralateral and other paws. In another embodiment, the application program 12 is configured or programmed to generate and display laterality weight bearing/impulse/other kinematic or kinetic gait data percentage values, fore/rear limb weight bearing percentage values, and individual weight bearing percentage values.

In an embodiment, the application program 12 is configured or programmed to support creating and storing tests or trials of specific animals that are named or identified, including receiving start and stop signals via input to the computing device, and to compute and generate statistical data such as average values during the trial and/or trend values during the trial, with respect to any of the data values that are identified above.

In an embodiment, the application program 12 is configured or programmed to obtain the geo-location data from the GPS transceiver 18 and to calculate velocity values that represent a velocity of animal 2 over time. Velocity values may be generated and stored in association with weight bearing values and/or other kinetic/kinematic values that are identified from the sensors 82 of the footwear elements 8 at the same approximate time and therefore the application program 12 may be configured or programmed to calculate and display a change in weight bearing at different speeds of the animal 2, with or without a representation of a time axis.

In an embodiment, the application program 12 is configured or programmed to access camera 16 that is integrated in or coupled to the computing device 10 and to cause initiating a video recording at the same time or in association with starting testing or a trial. For example, when the computing device 10 is a mobile computing device such as a smartphone or tablet computer having an integrated camera 16, the application program 12 is configured or programmed to programmatically call or signal a service, function or primitive of the operating system 14 of the computing device to access the camera and/or trigger a camera recording function. Such a call or signal may be generated when a test or trial starts, or asynchronously with respect to the initiation of data gathering. The particular way of triggering a video recording is not critical.

In an embodiment, the application program 12 is configured or programmed to obtain a timestamp value, based on a system clock of the computing device 10, at the time that the video recording starts and to store the timestamp value in association with a dataset representing a continuous set of data from sensors 82 that is collected during a test, trial or other period that coincides with the recording. In this manner, the application program 12 is configured or programmed to associate a start of the video recording with a particular set of first data values or starting data values that correspond to the start of the video recording.

Consequently, the application program 12 also may be configured or programmed to replay the video recording on a display device of the computing device 10, in synchronization with continuous display of a changing graph of the data that was gathered at the same time as the recording occurred. In an embodiment, the application program 12 is configured or programmed to detect when the sensor data indicates asymmetry, thereby indirectly indicating asymmetry in weight bearing on different limbs of the animal 2, and to generate and display a marker, alert, notification or other signal in a portion of the computer display. The marker, alert, notification or other signal may be displayed intermittently as asymmetry is detected or not detected, and may be visually or graphically superimposed over the replayed video recording of the animal 2.

Implementation Example—Process of Use

In an embodiment, the system described herein is used as part of a diagnostic process that is capable of reporting an assessment of lameness in real time, that is, at the same time that an animal is walking or moving while wearing the footwear elements. In one approach, the footwear elements are fitted to the animal, optionally including applying or turning on power to the sensors or footwear elements. Before or afterward, the wireless data relay device, if used, is affixed to the animal, such as by attaching a collar or other wearable item. The application program is launched on a compatible computing device, and establishes wireless communication with the sensors and optionally with the wireless data relay device; in this manner, the application program begins requesting, obtaining or receiving a stream of data values either directly from the sensors or indirectly via the data relay device. Data may comprise raw sensor values indicating pressure or force, or transformed data indicating weight, together with unique identifiers of which limb, paw or sensor reported the data.

In an embodiment, the system is initially calibrated using one or more external devices. For example, the animal may be fitted with the footwear elements initially. The sensors for the footwear elements may be initially zeroed out with the animal lying down or in a position where little to no force is placed on the sensors in the footwear elements. The animal may then be placed on a digital scale to obtain weight measurements while a stream of data values is obtained from the footwear elements. The stream of data values representing force from each of the footwear elements may be aggregated and compared to weight data from the digital scale. The system may then be calibrated such that the total forces from the footwear elements aggregate to the measured weight of the animal.

Weight values may be manually input from reading of the scale and/or automatically sent from the scale to an external device. For example, the scale may include a proximity sensor which is configured to detect proximity of the wireless relay device 4. The scale may identify an account of wireless relay device 4 based on data transmitted from wireless relay device 4 and send weight data to a computing device associated with the account and/or to a server system such that the data can be associated with the account. Additionally or alternatively, a tag worn by the animal may comprise a scannable code, such as a bar code or QR code which can be scanned by a scanner on the scale to associate weight data with the animal.

In a typical usage scenario, the animal may be caused to walk a short distance over any available surface and in any available location. A pad, plate or other specialized surface is not required. As an example, an owner, caretaker or animal healthcare provider may lead or call the animal to cause walking. During gait of the animal, the sensors continuously produce output data indicating pressure, force, and/or other kinematic data or kinetic data such as acceleration or max velocity or provide data in response to signals, polls or calls by the data relay device or the computing device. In an embodiment, the application program is configured or programmed to concurrently display a graph, graphical user interface, or other visual output. In various embodiments, the visual output may comprise raw sensor values indicating pressure or force, or transformed data indicating weight or impulse, together with unique identifiers of which limb, paw or sensor reported the data. Or, the visual output may comprise graphs, charts or tables (graphical representation of current gait overlaid on breed/conformation-specific representations or historical ones) specifying either raw data or transformed data, alone or in conjunction with a video player window that shows a video recording of the animal as the animal is moving.

In some embodiments, display of visualized data from sensors 82 may be deferred until after a period of initialization, calibration or preparation. That is, the application program 12 may be programmed to discard the first few seconds of data from sensors 82 on the assumption that initial gait will be irregular or more likely to contain anomalous data.

In some embodiments, the application program 12 is configured or programmed to apply algorithmic analysis to the raw data or transformed data and to generate and display one or more diagnostic suggestions in the visual display of the computing device 10. The diagnostic suggestions may comprise, for example, a list of possible diagnoses that are associated with the particular species of the animal 2 and the data values that were collected. The application may additionally display one or more of the maximum velocity and/or other measured values, velocity versus time, number of activated sensors of a sensor array, length of time in various gaits, changes in symmetry during gaits, gait changes, changes in gait characteristics over time, possibilities of bilateral disease based on changes in limb values, diseases or pathologies affecting forelimb versus hind limb, compensatory changes in kinetic values, and/or a degree of certainty of diagnosis based on the received values.

Implementation Example—Functional Overview

Figure 2:
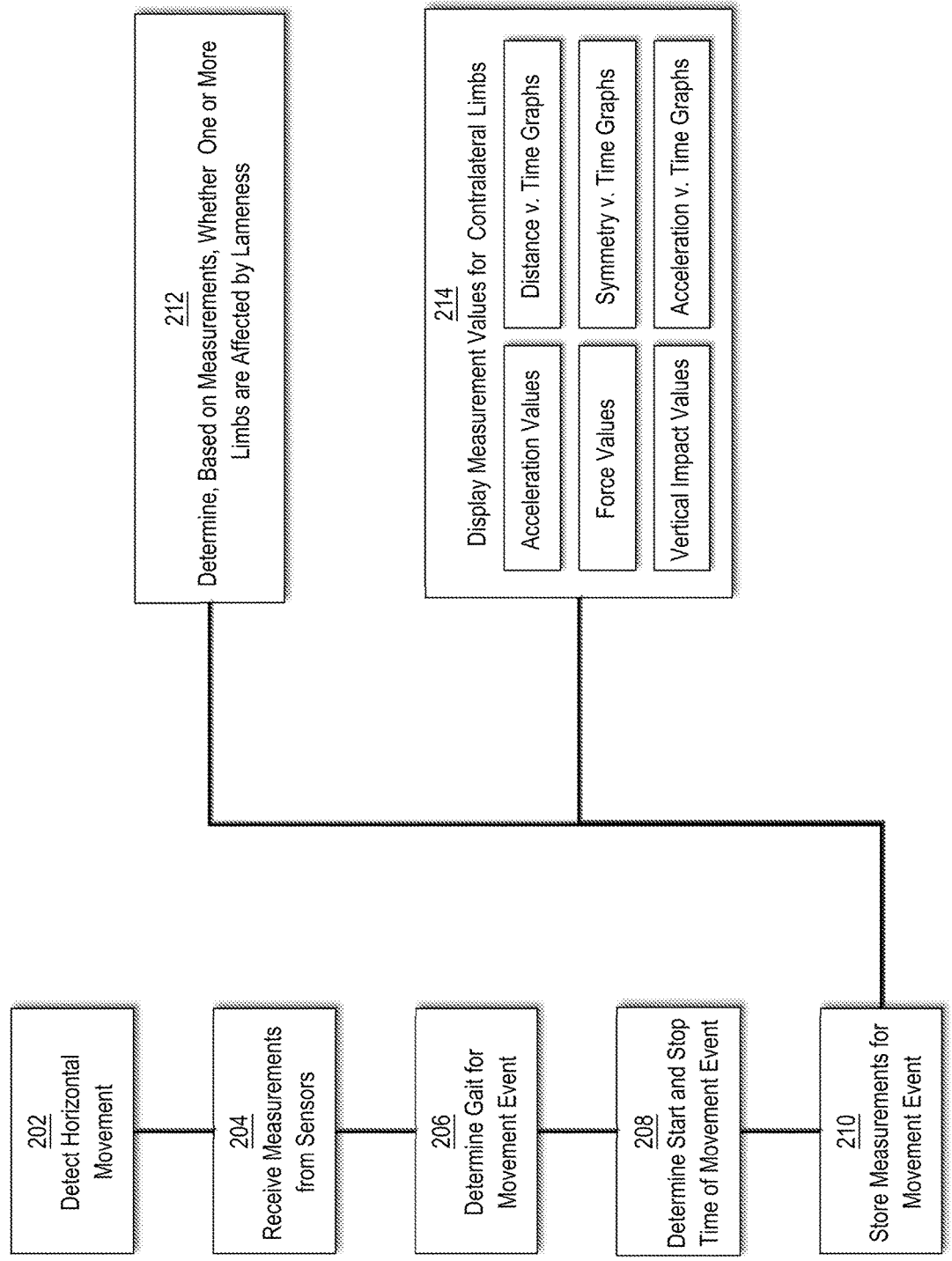
FIG. 2 illustrates an example operational flow of an application program.

The systems described herein may be used to detect lameness during one or more movement events. Movement events may refer to discrete instances of movement or non-movement for an animal. For example, movement events may be separated by instances of the animal standing, sitting, lying down, or a change to a different type of movement event. Additionally and/or alternatively, movement events may refer to discrete instances of movement at a particular gait. Thus, if an animal is initially moving in an asymmetrical walking gait and shifts to a running trot, the time spent in the walking gait would be considered a first movement event while the time spent in the running trot would be considered a second movement event. FIG. 2 illustrates an example operational flow of an application program.

At step 202, the system detects horizontal movement. For example, the one or more sensors may include an accelerometer, gyroscope, and/or inertial measurement unit which sends acceleration data to the wireless data relay device. Additionally or alternatively, one or more sensors attached to the wireless data relay may include an accelerometer which provides data to the wireless data relay. The wireless data relay device may comprise digitally programmed logic which is configured to determine whether the acceleration data indicates horizontal movement. For example, acceleration in a direction perpendicular to the constant downward acceleration as measured by the accelerometers and/or other gravitometers may be identified as horizontal acceleration and used to compute horizontal velocity of the animal. Additionally and/or alternatively, the wireless data relay device may send acceleration data to an external computing device which is programmed or configured to determine whether the acceleration data indicates horizontal movement. Thus, as used herein, determinations made by the system may be performed at the wireless data relay and/or at an external computing device.

In an embodiment, the one or more sensors detect horizontal movement prior to sending data to the wireless data relay device. For example, the sensors may be initially inactive when at rest. In response to detecting motion, the sensors may begin transmitting measurement data to the wireless data relay device. Additionally and/or alternatively, the determination may be based on receipt of external input. For example, an external computing device may receive user input requesting recording of a movement event. In response to the request, the system may begin storing measurement data from the one or more sensors.

At step 204, the system receives measurements from the sensors. For example, the system may continuously receive measurements of acceleration, vertical impact, vertical impulse, pressure, position, and or other motion related values. The measurements may be received as time series data which include temporal data in conjunction with the measured accelerations, vertical impulses, pressure, and/or position. The measurements may be continuously sent from the sensors prior to the movement event and/or sent from the sensors in response to a detection of a movement event.

At step 206, the system determines a gait of the animal. For example, the system may identify measurements from sensors on each limb. Based on the measurements, the system determines motion of each limb. Based on motion and placement of each limb in relation to the other limbs, the system may determine the gait and/or movement type of the animal. Methods for determining gait are described further herein.

At step 208, the system determines a start and stop time of a movement event. The start and stop times may be determined based on input from an external computing device, based on initiation/cessation of horizontal motion, and/or beginning/ending of movement at a particular gait. For example, if a running gait is defined as a movement where the limbs spend a greater amount of time off the ground than on the ground, then the beginning of the movement event for a running gait may be determined to be a point in time where the amount of time each limb spends off the ground exceeds the amount of time the limb spent on the ground prior.

At step 210, the system stores measurements for movement events. For example, the system may store acceleration, vertical impulse, and/or pressure/force measurements for each of the limbs between the identified start time of the movement event and the identified end time of the movement event. The system may additionally compute one or more values from the measurement data. For example, using the acceleration and temporal data, the system may compute velocities with respect to time and/or positions with respect to time. Additionally and/or alternatively, the system may compute averages, maximums, and/or minimums of measured values, such as acceleration, vertical impact/impulse, and/or pressure.

At step 212, the system determines, based on the received measurements, whether one or more limbs are affected by lameness. For example, the system may compare measured and/or computed values for contralateral limbs to determine whether one or more limbs are affected by lameness. Methods for comparing measurement values produced by the system are described further herein. At step 214, the system displays measurement values for contralateral limbs. For example, the system may display any of acceleration values, force values, vertical impulse values, distance v. time graphs, symmetry v. time graphs, and/or acceleration v. time graphs on a client computing device. Methods for displaying measurement values and/or computed values on a client computing device are described further herein.

Implementation Example—Measurements and Algorithms

In an embodiment, the system uses one or more force sensors, such as load cells, to produce measurements of force for each of a plurality of limbs of the animal. The system may store average force for each limb and/or peak ground reaction force for each limb. In an embodiment, the system stores peak force for each period in which weight is placed on a limb. Thus, times when the animal is lifting a limb may act as buffers between measurements of force. The system may additionally store and/or display relative force values. For example, the system may determine average force for each limb over a particular period of time. The system may compute, for each limb, the force relative to total force. Thus, if an animal has four limbs and applies force equally to each limb, the system may compute the relative force for each limb as 25%.

In an embodiment, the system uses force, pressure, impulse, or other kinematic values to determine whether a limb is affected by lameness. For example, the system may compare average force exhibited by contralateral limbs. Thus, the front left limb may be compared with the front right limb while the rear left limb is compared with the rear right limb. If the difference between average force values is greater than a stored threshold value, the system may determine that the limb with the lower force values is suffering from lameness. The threshold value may be an absolute value, a value computed as a function of the animal's weight, and/or a percentage difference. As an example, the system may determine whether the difference between average forces for contralateral limbs is greater than or equal to one fortieth of the animal's weight. As another example, the system may determine if the difference between relative forces for contralateral limbs is greater than or equal to a 3% difference.

In an embodiment, values for the animal are compared to average values for similar animals. For example, a cloud server computer may store movement data received from a plurality of sensors on a plurality of animals. The data may be accompanied by data defining the animal type, breed, and/or weight. For example, an application executing on the computing device may be used to define traits of the animal, such as breed and type. The data may be aggregated for each animal type so that the data can be compared with other animals of the same type. For example, the system may compare measured data for an Italian greyhound, such as force, vertical impulse, and/or pressure, with stored measurements from other Italian greyhounds.

In an embodiment, measured forces for the limbs are used to determine whether a limb is in the air or is incident to the ground. For example, when the vertical force incident on the sensors is less than or equal to a threshold value, the system may determine that the limb is aloft. When the vertical incident on the sensors exceeds the threshold value, the system may determine that the limb is on the floor. Using the data indicating whether the limb is aloft or on the floor, the system may determine whether a limb is affected by lameness. For example, the system may compare time spent aloft or time spent on the ground for contralateral limbs. If the difference between time spent in the air or on the ground for the contralateral limbs is greater than a threshold value, the system may determine that the limb with the greater amount of time in the air is being affected by lameness. Additionally or alternatively, if the difference between time spent on the ground for the contralateral limbs is greater than a threshold value, the system may determine that the limb with the lesser amount of time on the ground is being affected by lameness.

Measured and/or computed data indicating when each limb is on the ground may be used to determine the gait of the animal in an embodiment. The system may store data identifying each gait as a function of a pattern of time each limb spends on the ground versus aloft compared with the contralateral and other limbs. For example, a trot may be defined as occurring when diagonally opposite limbs are moving in unison. Thus, the front left leg and rear left leg are both aloft and on the ground at the same time. A gallop may be defined as occurring when contralateral limbs are lifted/placed on the ground in succession, such that time spent aloft and on the ground for contralateral limbs overlap but do not exactly match. As described above, a run may be defined as occurring when the time limbs spend aloft exceeds the time the limbs spend on the ground.

By matching patterns of motion, the system may determine the gait of the animal during a movement event. The system may determine changes in patterns of limb movement to determine changes in gait. For example, the system may identify a first pattern of limb movement over a first period of time. The system may determine points in time where the limb movement does not match the prior pattern. For example, if a first gait is a bound where contralateral limbs move in unison, then the system may determine when the limbs stop moving in unison as a transition to a different pattern. The system may then identify a next pattern of movement. In an embodiment, the system only identifies a gait if a pattern is repeated for greater than a threshold period of time and/or greater than a threshold number of movement cycles. For example, the system may only identify gaits for movement patterns that last longer than three seconds. Additionally and/or alternatively, the system may only identify gaits for movement patterns that repeat in at least three cycles of movement of all limbs.

In an embodiment, the system measures an amount of time spent in each gait. The system may additional compute changes in gait duration over time. For example, the system may store the data identifying the amount spent in a particular gait for a plurality of movement events over time. The system may then compute a change in gait over time value which measures a change in the amount of time an animal spends in the particular gait over time. The change in gait over time may indicate changes in the animal's movement patterns, such as by showing that an animal has begun running less over the past few months than in the years prior, thereby indicating a change in the animal's physiology and/or lifestyle.

Additionally, the system may identify a change in the use of abnormal gaits over time. For example, the system may compute a percentage of time that is spent at each gait, such as 4% of time spent at a bunny hop over a period of time, such as days, weeks, months, or years. If the system detects a change in use of abnormal gait, such as the percentage of time spent at the gait over a recent period of time being greater than two standard deviations from the average amount of time spent at the gait, the system may identify the change and send data identifying the change to the computing device.

In an embodiment, the system uses movement data and/or position data from the sensors and/or the wireless data relay to determine distance traveled by individual limbs and/or by the animal. Distance traveled may be stored for individual movement events and/or as aggregate values. For example, the system may store data describing total distance traveled, total distance traveled for each gait, total distance traveled in movement events where lameness was detected, and/or other aggregate distance values.

Distance values may be displayed on the client computing device and/or used to compute additional values. For example, the system may compute an average velocity for each limb as the quotient of the distance traveled and the time during which the distance was traveled. In an embodiment, the system computes average for each limb while the limb is aloft. For example, the system may divide a value indicating a distance traveled when a limb is aloft from the amount of time the limb is aloft. In an embodiment, the system uses computed velocities to determine whether a limb is affected by lameness. For example, if the difference in average velocities and/or maximum velocities of contralateral limbs is greater than a stored threshold value, the system may determine that the limb with the lower velocity is being affected by lameness.

In an embodiment, the sensors measure acceleration values for each limb. For example, the sensors may include accelerometers which measure the acceleration of each limb during movement. The system may identify, for each limb, a maximum acceleration and a minimum acceleration. The minimum acceleration may comprise the maximum deceleration. The system may use the acceleration values to determine if a limb is affected by lameness. For example, if the difference in maximum acceleration between limbs is greater than a threshold value, the system may determine that the limb with the lower acceleration is being affected by lameness. Additionally and/or alternatively, the system may compare a combination of maximum acceleration and maximum deceleration between limbs. If the difference between maximum acceleration and minimum acceleration of a limb is greater than the difference between maximum acceleration and minimum acceleration for a contralateral limb by greater than a threshold value, the system may determine that the limb with the lower difference is being affected by lameness.

Measured acceleration values may also be used to compute velocities over time and/or maximum velocity. For example, the system may identify measurements of acceleration during a period of time where a limb is aloft. The system may average positive accelerations prior to a first measurement of deceleration. The system may compute a maximum velocity for the period of time as the average acceleration multiplied by total time in which the acceleration was positive. The maximum velocity may then be used to determine lameness as described above and/or determine position of the animal.

Measured values may be compared to historical values for the animal to indicate changes in the animal's behavior. Additionally or alternatively, measured values may be compared to average measured values for similar animals, such as animals of the same breed. For example, the wireless relay device and/or the computing device may send measurements for the animal to a server computer which aggregates measurements from multiple animals. In an embodiment, the measured values are associated with the type of animal, such as breed of dog identified during calibration and/or through input on the computing device. The aggregated measurements for different animals and/or breeds may be used to compute average values. The average values may then be compared against specific values for an animal in order to determine if the animal's movement is impaired.

The system may use one or more of the methods described herein to determine whether a limb is being affected by lameness. In an embodiment, the system identifies whether lameness was determined as originating from the stance phase or the swing phase. For example, the system may determine lameness based on acceleration while the limb is not impacting the ground as one method and determine lameness based on the ground reaction force when the limb is impacting the ground as a second method. The system may store data indicating which method resulted in a determination of lameness, thereby allowing for differentiation between different potential causes, such as fractures, ligament disease, infection, or osteoarthritis which would affect load bearing, and tendonopathies or myopathies which would affect motion.

The system may use measured values to compute lameness caused by different underlying conditions. For example, measured values may be used to determine instances of bilateral disease by identifying a drop in symmetrical plantar ligament vertical impact and a large increase in transverse ligament vertical impact. The system may additionally identify combinations of lameness by comparing measured values to different permeations of lameness combinations, such as long transverse ligament lameness coupled with bilateral plantar ligament lameness.

While methods described herein relate to identifying lameness based on differences in contralateral limbs, the methods described herein may additionally be used to determine lameness based on historical differences between forelimbs and hindlimbs. For example, some diseases affect both hind limbs, thereby reducing the effectiveness of comparisons of contralateral limbs. The system may store data identifying historical measurements for each limb and compare the differences over time. For example, if an animal historically places 60% of its weight on its front limbs and 40% on the rear limbs, then the system may identify symmetrical thoracic limb lameness when the animal begins placing 50% of its weight on its front limbs and 50% on the rear limbs.

In embodiments, the wireless data relay device may be programmed or configured to produce measurements that differ from the sensors on the limbs. For example, the wireless data relay device may measure displacement for different periods of time, including for different movement events, different gaits, movement events where lameness was detected, and/or predefined periods of time such as hours, days, weeks, and/or months. The wireless data relay may also measure time spent at different gaits, overall acceleration of the pet, and overall velocities of the pet. The system may compare data received from the wireless relay device with data received from the sensors. For example, the system may compare individual velocities from the sensors with the velocity of the animal as measured through the wireless data relay device.

Implementation Example—Display

Figure 3:
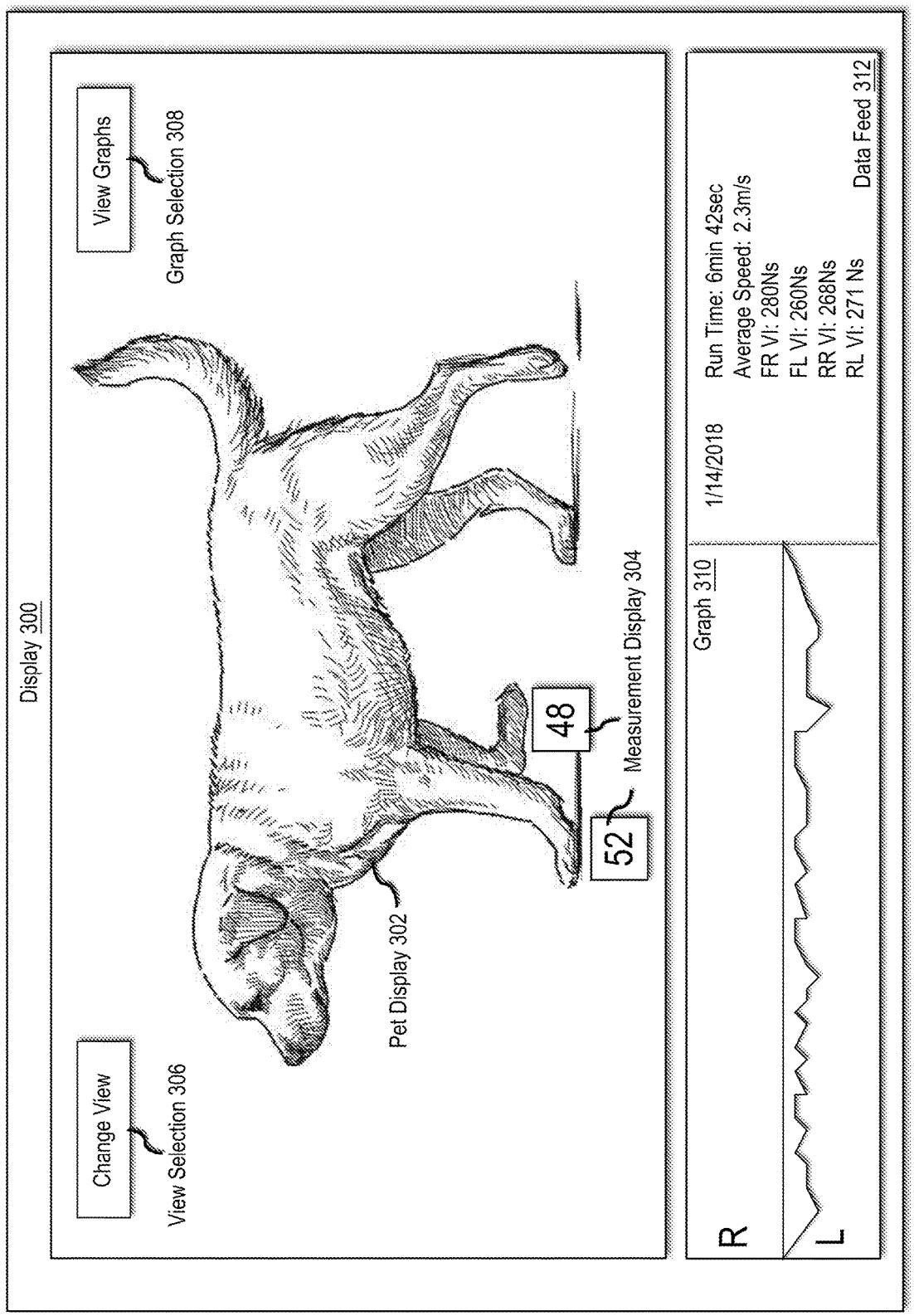
FIG. 3 illustrates an example graphical user interface (GUI) with example visualization of lameness data.

In an embodiment, the system generates a display on a client computing device which is used to view captured and/or computed data regarding the animal. FIG. 3 illustrates an example graphical user interface (GUI) with example visualization of lameness data. Display 300 comprises pet display 302, measurement display 304, view selection 306, graph selection 308, graph 310, and data feed 312.

Pet display 302 comprises an image of the animal which is being monitored. Pet display may include a generic outline of an animal. For example, if the monitored animal is a dog, the system may display a generic outline of a dog. In an embodiment, the system uses images of the animal being monitored. For example, an application running on a client computing device may initially request images of the monitored animal from one or more angles while the pet is standing, walking, and/or otherwise upright so that one or more limbs are visible. The application may utilize a camera on the client computing device, such as an internal camera of a smart phone, and/or request upload of an image. When the application receives a requested image, the application may request identification of individual limbs, such as through use of a cursor and/or touch screen. The application may then store the image of the animal with metadata describing the view of the animal, such as front view or side view, and locations of the one or more identified limbs.

Measurement display 304 comprises a display of one or more measurements and/or computed values for individual limbs. Values displayed in measurement display 304 may include absolute and/or relative vertical impulse, acceleration, velocity, and/or time limb spends on the ground/aloft. The system may be programmed or configured to display one type of value and/or to switch between value types based. For example, the interface may include an option to toggle between displaying vertical impulse, acceleration, velocity, and or time limb spends on the ground/aloft. Various displays may show different limbs. For example, one display may show only the front limbs while a different display shows only rear limbs.

The measurements of measurement display 304 may be displayed over the individual limb to which the measurement refers. For example, a value displayed over the right front limb may be a measurement and/or computed value for the right front limb. In the example of FIG. 3, the system displays values representing a percentage of vertical impact on the front legs for each limb. Thus, the front right limb was measured to produce 48% of the vertical impact on the front limbs while the front left limb was measured to produce 52% of the vertical impact on the front limbs.

In an embodiment, the display may additionally identify the gait of the animal during the movement event. For example, the gait of the animal may be displayed above an image of the animal or superimposed on an image of the animal. In embodiments where the interface displays data regarding the pet in real time, the display may update to show the new gait of the animal when the device determines that the gait of the animal has changed.

The gait of the animal may be used to determine when to begin capturing data to be relayed to the computing device. For example, the system may determine whether a steady gait has been reached, such as by identifying a repetition of a gait over a particular number of strides. Additionally or alternatively, a calibration step may be performed where a specific gait for an animal is recorded during movement of the animal. The system may identify the specific gait as a "usual" gait for the animal and begin recording capturing data to be relayed to the client computing device when the animal reaches the "usual" gait.

View selection 306 may be displayed on the graphical user interface for changing the view of the animal through the graphical user interface. For example, the system may include multiple views of the pet, including a front view, a side view, and a back view. The system may switch between the views for comparisons of different limbs. Additionally, the system may switch between different types of views.

Figure 4:
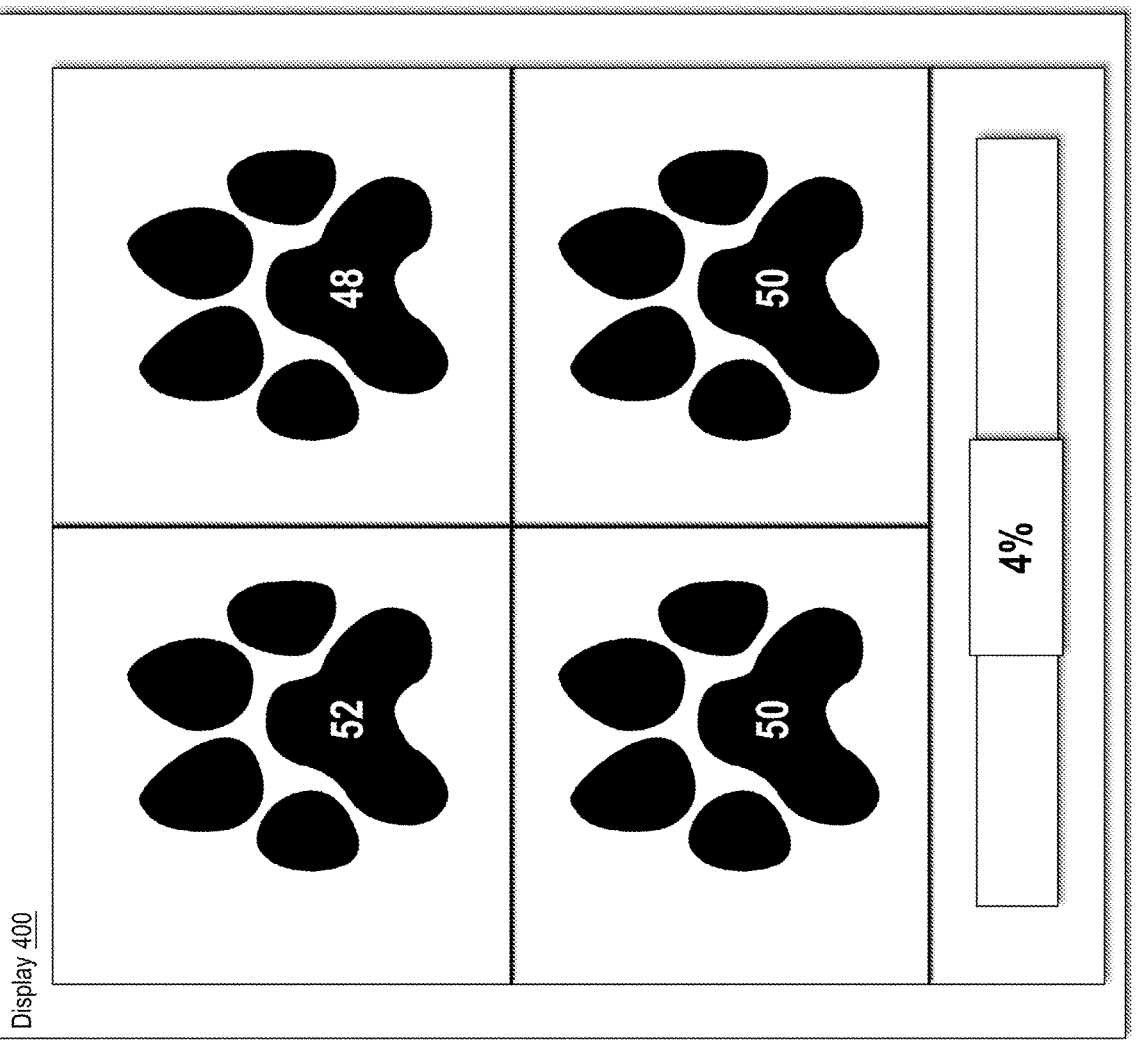
FIG. 4 depicts a graphical user interface depicting comparisons of data for the limbs of an animal

For example, FIG. 4 depicts a graphical user interface depicting comparisons of data for the limbs of an animal. The display of FIG. 4 may be selected as a different view and/or may act as an alternative view for the system. Display 400 includes depictions of paws for each limb and a value for each paw indicating one of the measurements and/or computations for the corresponding limb. The view of FIG. 4 allows for easy comparison of the individual limbs. Additionally, the view may include a slider which visually indicates asymmetry of the limbs. For example, the slider at the bottom of the display of FIG. 4 is displayed as being balanced slightly to the left to indicate that more pressure is being placed on the left front limb than the right front limb. Additionally, the slider includes a value indicating the percentage difference between the value for the left front leg and the right front leg.

In an embodiment, a display similar to FIG. 4 may be used to show a center of gravity based on load bearing. The center of gravity may refer to the two-dimensional center of downward force or pressure. For example, the system may compute a location of the center of gravity of the animal based on the load placed on each foot. Thus, if 60% of an animal's load is placed on the front limbs, 40% on the rear limbs, and no asymmetry exists between contralateral limbs, the icon may be placed slightly higher than the center point between the four displayed paw prints. A video display may additionally depict the change in the center of gravity over time by depicting movement of the icon from indicating a center of gravity initially to indicating the recent measurement of center of gravity.

Returning to FIG. 3, graph selection 308 comprises an option for viewing different graphs. The graphs may include line plots depicting changes in values over time with respect to one or more limbs. For example, a line plot may include a line for the front left limb and a line for the front right limb. Additionally and/or alternatively, a graph may include a single line denoting differences in symmetry for different values. Thus, when the values are the same for contralateral limbs, the line may be centered in the graph. When the value for a first limb begins exceeding the value for its contralateral limb, the line in the graph may begin moving towards the side representing the first limb.

Differences in symmetry may additionally be captured for different gaits and displayed through the computing device. For example, the system may determine an average symmetry difference value for each gait over a period of time, such as a week. The system may display the different symmetry values, thereby indicating which gaits have the higher impact on the symmetry of the animal.

Acceleration values collected over different periods of time may be used to generate graphs of maximum acceleration versus time for each limb. A graph depicting changes in maximum acceleration over time allows the system to visually indicate to a user the changes in the animal's movement over time and to indicate times where the variance between limbs was particularly pronounced. Vertical impact versus time graphs may additionally be used to display changes to the animal's movement with respect to time. Graphs may be displayed individually and/or overlaid on each other. For example, a display may show side by side superimposed graphs of vertical impulse, maximum velocity, and acceleration versus time.

A distance versus time graph may visually indicate when an animal is moving one limb slower than the other, as the graph would visually indicate that one of the limbs took a longer amount of time to cover a same distance as a contralateral limb. The distance versus time graph thus visually indicates that an animal has been moving one limb faster than another at different points in time. Additionally, the distances versus time graph may be used to provide velocities of the individual legs which can be compared to the velocity of the animal.

The system may also display a symmetry versus time graph which visually depicts differences between the limbs over time. For example, a symmetry graph for maximum acceleration would show differences in the accelerations of contralateral limbs over time. Thus, if at a time A, both limbs had the same acceleration, the graph would show neutral symmetry for time A. If at time B, the system computed a 5% difference in acceleration between the limbs, the graph would depict a 5% difference at time B.

In an embodiment, the system visually identifies portions of a graph that indicate lameness in the animal. For example, the system may highlight a portion of an acceleration graph where the differences in maximum acceleration between two contralateral limbs exceeded a stored threshold value. By visually altering the graph based on a determination of lameness, the system generates a dynamic graphical user interface which is effective in not only identifying lameness, but also displaying evidence of lameness.

Graph 310 comprises a graph that is displayed with interface 300. Graph 310 may include any of the graphs described above. In FIG. 3, graph 310 is a graph depicting relative values over time. Thus, as the animal begins favoring a particular leg, the line of the graph begins moving away from center. The graph of 310 may be a fixed graph type and/or a changeable graph. Thus, a user may select a different graph type to be displayed in display 300.

Graph 310 and measurement display 304 may be based on the totality of data gathered, specific instances of data gathered, and/or most recent instances of data gathered. For example, measurement display 304 may depict overall averages of vertical impact of the limbs while the graph 310 displays changes of vertical impact on the limbs over time. As another example, the system may display measurement data 304 and graph 310 based on a current and/or most recent movement event. For a current movement event, the system may continuously update graph 310 and measurement 304 based on newly measured values.

In an embodiment, the graph comprises a visual representation of differences between current values and past values. For example, an overlaid bar graph may depict pressures placed on each limb currently in one color and average pressures placed on each limb in the past in a different color, thereby depicting a visual indication of the changes of the animal over time.

In an embodiment, the system displays options for selecting different time periods, gaits, and/or tracked values for graph 310 and/or measurement display 304. For example, in response to a selection of a "trot" gait, the system may display average values obtained during a trot gait in measurement display 304 and changes in the values during the trot gait in graph 310. As another example, the system may respond to a selection of a particular movement event and/or a selection of a particular time period by displaying data values for the movement event and/or particular time period.

Data feed 312 comprises a display of data values. Data feed 312 may include data values for movement events, periods of times, and/or different gaits. The data feed 312 may include an identification of a time period, movement event, and/or gait for each set of values. For example, in FIG. 3, data feed 312 comprises data values for a run performed on Jan. 14, 2018. The data values include the run time for the pet, the average speed of the pet, and the peak and average vertical impulse for each limb. Data feed 312 may include a scrollable interface with additional tracked movement events and data values for the other events. In an embodiment, the interface may be filtered to display only events in which lameness was detected. In an embodiment, data feed 312 comprises values that correspond to graph 310 and data/or measurement display 304.

The data feed 312 may additionally depict differences in values from average values for the animal. For example, the system may use aggregated data to compute average acceleration values for each limb at a particular gait. During a movement event at the particular gait, the system may compute differences between current acceleration for each limb and average acceleration for that limb. The system may display variation values calculated from average values and current values in order to depict changes in normal behavior. By displaying differences between average values and values for a particular movement event, the system allows a user to determine whether the animal is behaving abnormally.

In an embodiment, the data relay device additionally includes a GPS transceiver and/or other positioning identification device. The system may store data identifying location of the animal for different measurement values. Using the measurement values and location data, the system may determine locations where measurements change in the movement of the animal. For example, the system may identify a location where, during a movement event, the difference in vertical impacts for contralateral limbs is greater than a threshold value. The system may display, on a map, an icon indicating the location at which, during the movement event, the difference occurred. The displayed location data may be useful for determining how long to walk a pet. For example, a pet owner may view the map to determine how long the pet owner walked the pet before the pet's limb began to function poorly, thereby allowing the pet owner to adjust walks to match the capabilities of the pet.

Different map displays may demonstrate changes in animal over time, such as for evaluating recovery, responses to medication, and/or changes in energy. For example, a map display may include icons identifying each location where, during a movement event, asymmetry between contralateral limbs surpassed the threshold value. Each icon may additionally indicate a time or date when the movement event took place. Thus, an owner may track changes to the distance an animal is able to walk before movement is impaired.

Implementation Example—Additional Embodiments

In an embodiment, the wireless relay device includes one or more force sensors. For example, the wireless relay device may be placed in a collar for an animal, at a leash attachment site, and/or at another position on the animal. The force sensors may be used to track forces from pushes and pulls originating from a leash attached to the collar. Additionally and/or alternatively, force sensors on a leash may send measurement data to the wireless data relay device. Forces from the leash may be used to augment the recording of movement as a portion of the force on one of the limbs would be caused by the pull of the leash.

Additionally and/or alternatively, the wireless data relay device may be configured to detect proximity of the leash to the collar or attachment link. Based on proximity of the leash to the collar and/or data indicating force on the leash, the system may store data identifying the movement event as an event which involves the pet owner. The system may use this data to track how long the owner spends with the pet and/or how often the user takes the pet for walks.

In an embodiment, the system is programmed or configured to interact with one or more external devices. For example, the wireless data relay device may connect to one or more devices that monitor a food bowl and/or water bowl. The system may use the wireless data relay device and the food and/or water bowl to compute food and/or water intake for the animal. A measurement device in a food and/or water bowl may initially measure how much food and/or water is in the bowl. For example, a scale on the bowl may weigh food and/or water in the bowl.

A sensor in the food and/or water bowl may be configured to detect close proximity of the wireless data relay device and/or a sensor in the wireless data relay device may be configured to detect close proximity of the food and/or water bowl. The sensors in the food and/or water bowl may send data to the wireless data relay device identifying the weight of the food and/or water in the bowl prior to detection of close proximity of the wireless data relay device.

When the food and/or water bowl ceases to be in close proximity to the wireless data relay device, the sensors in the bowl may send a second measurement of the weight in the food and/or water bowl to the wireless data relay device. Additionally and/or alternatively, one or more processors communicatively coupled to the sensors in the food and/or water bowl may be programmed or configured to compute a difference in weight of the food and/or water and send the difference in weight to the wireless data relay device. The system may store a total food and/or water intake for the animal over one or more periods of time based on the differences in weight of the food and/or water in the bowl prior to the detection of close proximity of the animal and after detection of close proximity of the animal.

Monitoring of the food and/or water intake of an animal may be used to detect early symptoms of one or more problems. For example, if an animal's food intake drastically decreases, the system may determine that the animal is not eating and therefore may be sick. As another example, if an animal's water intake drastically increases, the system may determine that the animal is suffering from one or more pathological conditions. Similar systems may be implemented with a litter box to track a cat's frequency of urination and/or to detect other gastrointestinal problems.

In an embodiment, a food and/or water bowl uses the detection of the wireless data relay device to apportion food and/or water to the animal. For example, the system may store data identifying an amount of food that is healthy for the animal to eat. When the food bowl detects close proximity of the pet the food bowl may deposit an amount of food based on the data stored by the system indicating a healthy amount of food for the animal. Using these methods, a food bowl may release different amounts of foods to different pets based on detection of proximity of the different pets.

The food bowl may also comprise separate dispensers for separate foods, thereby allowing apportionment of different foods to different pets. Thus, if a first pet is on a diet and can only eat Food A while a second pet only eats Food B, the system may detect close proximity of the wireless data relay device attached to the collar of the first pet and, in response, dispense Food A to the first pet. Food that is not eaten by the pet when the system ceases to detect close proximity of the collar may be automatically covered, such as by a piece of hard plastic.

In an embodiment, the food bowls additionally include sensors for weighing a remaining amount of food. The system may be programmed or configured to send a warning when the remaining food has decreased beyond a threshold value. Additionally and/or alternatively, the system may automatically order food from one or more predetermined retailers in response to a determination that the remaining food has decreased beyond the threshold value.

In an embodiment, a similar system is implemented for monitoring medication dispensation. For example, a medicine dish may include a bowl or container for the medicine and a scale. The system may determine whether medicine has been removed from the bowl based on a change in weight. For instance, the system may calibrate by weighing a single serving of the medicine and determine that medicine has been given to a pet when the weight of the medicine dish changes by the calibrated weight of the single serving. Medicine dispensation tracking may be used to correlate changes in movement with medicine application. For example, by tracking when the medicine was removed from the dish, the system may determine whether the asymmetry in the animal's movements decreases, increases, or stays the same shortly after medication.

The system may be configured to cause display of reminders on a computing device when medicine has not been removed from the medicine dish when medicine is supposed to be given to the pet. The system may be further configured to remove the reminder when the system identifies a change in weight that indicates that medicine was removed from the bowl.

In an embodiment, the system additionally tracks differences based on medicine use. For example, the graphical user interface may include an option for indicating that a medicine was administered to the animal. The system may compare values for vertical impact and/or acceleration after the medicine use with values for vertical impact and/or acceleration prior to the medicine use. By comparing values before and after medicine use, the system is able to use the sensors to record effects of various medicines.

Implementation Example—Computer Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

For example, FIG. 5 is a block diagram that illustrates a computer system 500 upon which an embodiment of the invention may be implemented. Computer system 500 includes a bus 502 or other communication mechanism for communicating information, and a hardware processor 504 coupled with bus 502 for processing information. Hardware processor 504 may be, for example, a general purpose microprocessor.

Computer system 500 also includes a main memory 506, such as a random access memory (RAM) or other dynamic storage device, coupled to bus 502 for storing information and instructions to be executed by processor 504. Main memory 506 also may be used for storing temporary variables or other intermediate information during execution of instructions to be executed by processor 504. Such instructions, when stored in non-transitory storage media accessible to processor 504, render computer system 500 into a special-purpose machine that is customized to perform the operations specified in the instructions.

Computer system 500 further includes a read only memory (ROM) 508 or other static storage device coupled to bus 502 for storing static information and instructions for processor 504. A storage device 510, such as a magnetic disk, optical disk, or solid-state drive is provided and coupled to bus 502 for storing information and instructions.

Computer system 500 may be coupled via bus 502 to a display 512, such as a cathode ray tube (CRT), for displaying information to a computer user. An input device 514, including alphanumeric and other keys, is coupled to bus 502 for communicating information and command selections to processor 504. Another type of user input device is cursor control 516, such as a mouse, a trackball, or cursor direction keys for communicating direction information and command selections to processor 504 and for controlling cursor movement on display 512. This input device typically has two degrees of freedom in two axes, a first axis (e.g., x) and a second axis (e.g., y), that allows the device to specify positions in a plane.

Computer system 500 may implement the techniques described herein using customized hard-wired logic, one or more ASICs or FPGAs, firmware and/or program logic which in combination with the computer system causes or programs computer system 500 to be a special-purpose machine. According to one embodiment, the techniques herein are performed by computer system 500 in response to processor 504 executing one or more sequences of one or more instructions contained in main memory 506. Such instructions may be read into main memory 506 from another storage medium, such as storage device 510. Execution of the sequences of instructions contained in main memory 506 causes processor 504 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 510. Volatile media includes dynamic memory, such as main memory 506. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 502. Transmission media can also take the form of acoustic or light waves, such as those generated during radio-wave and infra-red data communications.

Various forms of media may be involved in carrying one or more sequences of one or more instructions to processor 504 for execution. For example, the instructions may initially be carried on a magnetic disk or solid-state drive of a remote computer. The remote computer can load the instructions into its dynamic memory and send the instructions over a telephone line using a modem. A modem local to computer system 500 can receive the data on the telephone line and use an infra-red transmitter to convert the data to an infra-red signal. An infra-red detector can receive the data carried in the infra-red signal and appropriate circuitry can place the data on bus 502. Bus 502 carries the data to main memory 506, from which processor 504 retrieves and executes the instructions. The instructions received by main memory 506 may optionally be stored on storage device 510 either before or after execution by processor 504.

Computer system 500 also includes a communication interface 518 coupled to bus 502. Communication interface 518 provides a two-way data communication coupling to a network link 520 that is connected to a local network 522. For example, communication interface 518 may be an integrated services digital network (ISDN) card, cable modem, satellite modem, or a modem to provide a data communication connection to a corresponding type of telephone line. As another example, communication interface 518 may be a local area network (LAN) card to provide a data communication connection to a compatible LAN. Wireless links may also be implemented. In any such implementation, communication interface 518 sends and receives electrical, electromagnetic or optical signals that carry digital data streams representing various types of information.

Network link 520 typically provides data communication through one or more networks to other data devices. For example, network link 520 may provide a connection through local network 522 to a host computer 524 or to data equipment operated by an Internet Service Provider (ISP) 526. ISP 526 in turn provides data communication services through the world wide packet data communication network now commonly referred to as the "Internet" 528. Local network 522 and Internet 528 both use electrical, electromagnetic or optical signals that carry digital data streams. The signals through the various networks and the signals on network link 520 and through communication interface 518, which carry the digital data to and from computer system 500, are example forms of transmission media.

Computer system 500 can send messages and receive data, including program code, through the network(s), network link 520 and communication interface 518. In the Internet example, a server 530 might transmit a requested code for an application program through Internet 528, ISP 526, local network 522 and communication interface 518.

The received code may be executed by processor 504 as it is received, and/or stored in storage device 510, or other non-volatile storage for later execution.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. A lameness measurement system for a quadruped animal, comprising:
    a plurality of wearable footwear elements, each of the footwear elements comprising a housing that is configured to fit snugly on a paw of the animal, and each of the footwear elements comprising a sensor that is configured to detect and generate first data representative of pressure or force exerted by the paw upon a ground surface, and a first wireless transceiver that is configured for short-distance communication of the first data captured by the sensor; and
    a computing device comprising a second wireless transceiver that is configured to communicate wirelessly with the first wireless transceiver, and comprising a non-transitory computer-readable data storage medium storing sequences of instructions of an application program which when executed by the computing device cause: continuously obtaining the first data from each sensor of the footwear elements; continuously transforming the first data to produce a real-time data set indicating pressure or force of a paw of the animal relative to one or more other paws of the animal; determining, in real-time from the real-time dataset indicating the pressure or force of the paw of the animal relative to the one or more other paws of the animal, that the animal is being affected by lameness; and causing display of an analysis of lameness of the animal on a client computing device.

2. The system of claim 1, further comprising a wireless data relay device that is configured to receive the first data from the first wireless transceiver of each of the footwear elements via a first wireless networking protocol, to format the first data into messages of a second wireless networking protocol, and to transmit the messages using the second wireless networking protocol to the computing device, wherein the second wireless transceiver communicates wirelessly with the first wireless transceiver through the wireless data relay.

3. The system of claim 2, wherein the wireless data relay device is affixed to a collar of the animal.

4. The system of claim 2, further comprising one or more proximity sensors that are programmed or configured to detect proximity of a food and/or water bowl to the wireless data relay.

5. The system of claim 4, wherein the food and/or water bowl comprises one or more sensors configured to measure food and/or water in the food and/or water bowl prior to detection of the proximity of the food and/or water bowl to the wireless data relay and after cessation of the detection of the proximity of the food and/or water bowl to the wireless data relay.

6. A data processing method comprising:
continuously receiving, at a wireless data relay device, from a first wireless transceiver communicatively coupled to first one or more sensors attached to a footwear element worn on a first paw of an animal, first data representative of measurements of pressure or force exerted by the first paw upon a ground surface measured by the first one or more sensors;
continuously receiving, at the wireless data relay device, from a second wireless transceiver communicatively coupled to second one or more sensors attached to a footwear element worn on a second paw of the animal, second data representative of measurements of pressure or force exerted by the second paw upon a ground surface measured by the second one or more sensors;
determining a start time and a stop time of a movement event associated with the first data and the second data;
storing movement event data comprising at least the first data and the second data;
using digitally programmed logic to determine, in real-time while continuously receiving the first and second data, whether a limb of the animal is affected by lameness based, at least in part, on a comparison of the first data to the second data; and
displaying, on a client computing device, an indication as to whether the limb of the animal is affected by lameness.

7. The data processing method of claim 6, wherein determining whether the limb of the animal is affected by lameness comprises:
computing an average pressure or force exerted by the first paw and an average pressure or force exerted by the second paw between the start time of the movement event and the stop time of the movement event;
computing a difference between the average pressure or force exerted by the first paw and the average pressure or force exerted by the second paw; and
determining that the computed difference is greater than a stored threshold value and, in response, determining that the limb is affected by lameness.

8. The data processing method of claim 6, wherein displaying the indication as to whether the limb of the animal is affected by lameness comprises:
displaying, on a graphical user interface, an image representing the animal;
displaying, overlaid on a portion of the image corresponding to the first paw, a first value derived from the first data; and
displaying, overlaid on a portion of the image corresponding to the second paw, a second value derived from the second data.

9. The data processing method of claim 6, further comprising:
using the first data and the second data, identifying a particular gait of the animal; and
storing, as part of the movement event data, gait data identifying the particular gait of the animal during the movement event.

10. The data processing method of claim 9, wherein determining the start time and stop time of the movement event comprises:
using the first data and the second data, identifying a first time where the animal begins moving with the particular gait and storing the first time as the start time; and
using the first data and the second data, identifying a second time where the animal stops moving with the particular gait and storing the second time as the stop time.

* * * * *